United States Patent [19]

Gelfand et al.

[11] Patent Number: 4,711,845
[45] Date of Patent: Dec. 8, 1987

[54] PORTABLE TEMPERATURE-SENSITIVE CONTROL CASSETTE

[75] Inventors: David H. Gelfand; Frances C. Lawyer, both of Oakland, Calif.

[73] Assignee: Cetus Corporation, Emeryville, Calif.

[21] Appl. No.: 685,312

[22] Filed: Dec. 24, 1984

Related U.S. Application Data

[63] Continuation-in-part of Ser. No. 646,693, Aug. 31, 1984, abandoned, which is a continuation-in-part of Ser. No. 578,133, Feb. 8, 1984, abandoned.

[51] Int. Cl.[4] ............... C12P 21/00; C12P 19/34; C12N 15/00; C12N 1/20; C12N 1/00; C07H 17/00
[52] U.S. Cl. .................... 435/68; 435/172.3; 435/253; 435/317.1; 435/91; 536/27; 935/11; 935/29; 935/41; 935/43; 935/45; 935/73
[58] Field of Search ............ 435/68, 172.3, 240, 435/253, 317, 91; 935/11, 29, 41, 45, 43, 73, 27; 536/27; 260/112.5 R; 514/12; 530/351

[56] References Cited

U.S. PATENT DOCUMENTS

4,518,584 5/1984 Mark et al. ............... 435/112.5 X

FOREIGN PATENT DOCUMENTS

0041767 12/1981 European Pat. Off. ............. 935/41
0099084 1/1984 European Pat. Off. ............. 935/41

OTHER PUBLICATIONS

Roberts, TM. in *Promoters, Structure and Function* (EDS, LR Rodriguez and M. J. Chamberlin), pp. 452-461, 1982.
Rosenberg, M. et al. in *Methods in Enzymology*, vol. 101, Part C, pp. 123-138, 1983.
Wong, Em. *Proc. Natl. Acad Sci.*, vol. 79, pp. 3570-3574, 1982.
Shimatake, H. et al., *Nature*, vol. 292, pp. 128-132, 1981.
Remaut, E. et al., *Nuc Acids Res.*, vol. 11, pp. 4677-4688, 1983.
Remaut, E. et al., *Gene*, vol. 22, pp. 103-113, 1983.
Taniguchi, T. et al., *Nature*, vol. 302, pp. 305-310, 1983.
Goeddel, D. V., et al., *Nucl Acids Res* (1980) 8:4057-4074.
Scherer, G. F. E., et al., *Nucl Acids Res* (1980) 8:3895-3907.

*Primary Examiner*—Thomas G. Wiseman
*Assistant Examiner*—Jayme A. Huleatt
*Attorney, Agent, or Firm*—Kate H. Murashige; Albert P. Halluin

[57] ABSTRACT

Two types of convenient portable control cassettes for the expression of protein encoding sequences in procaryotes are disclosed. Both cassettes comprise the $P_L$ promoter from lambda phage, which is controllable by means of a temperature sensitive repressor, operably linked to the ribosome binding site for N-gene ($N_{RBS}$). In one embodiment, this cassette is bordered by restriction sites upstream of the $P_L$ promoter and immediately downstream from the $N_{RBS}$ permitting the insertion of a desired sequence containing its own start codon downstream from the cassette. The other embodiment contains an ATG start codon within the cassette and has a restriction site immediately 3' of the start codon.

26 Claims, 9 Drawing Figures

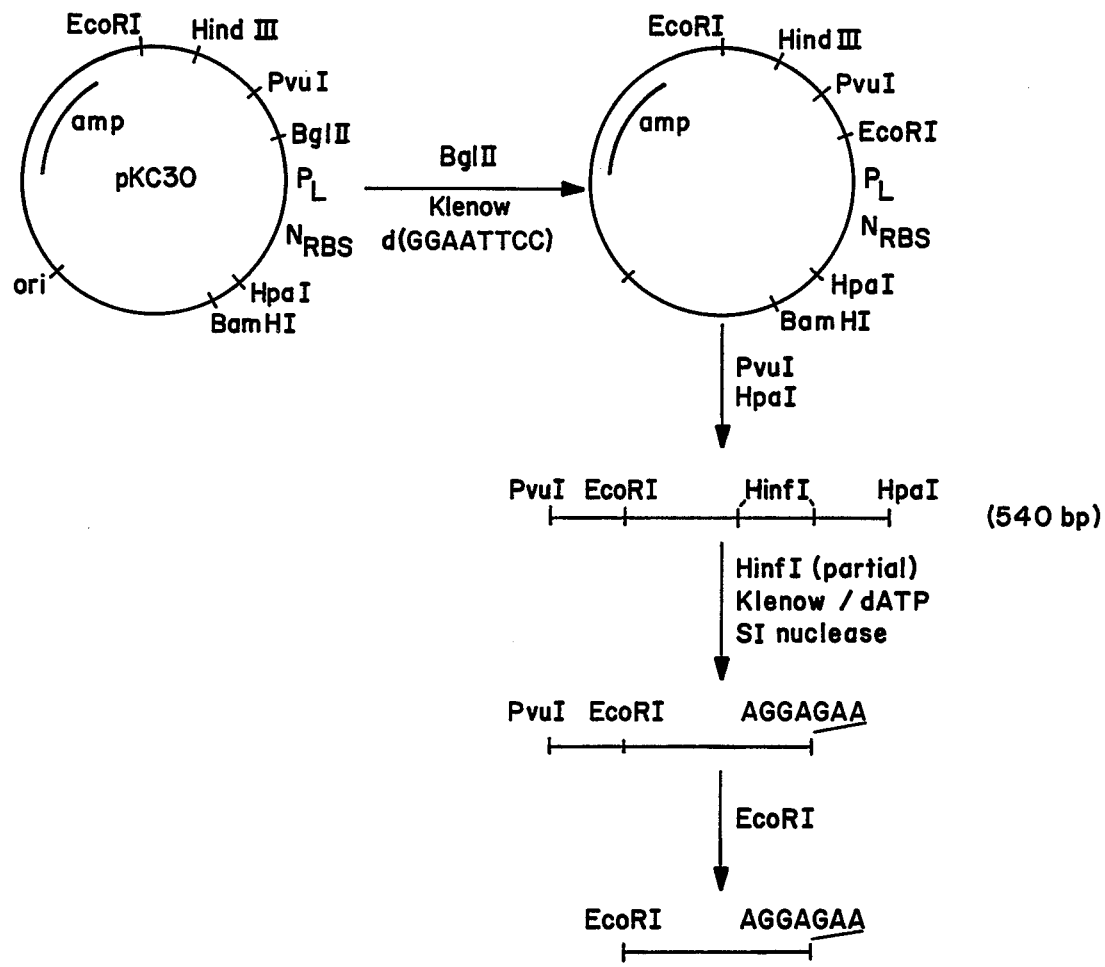
FIG._1.
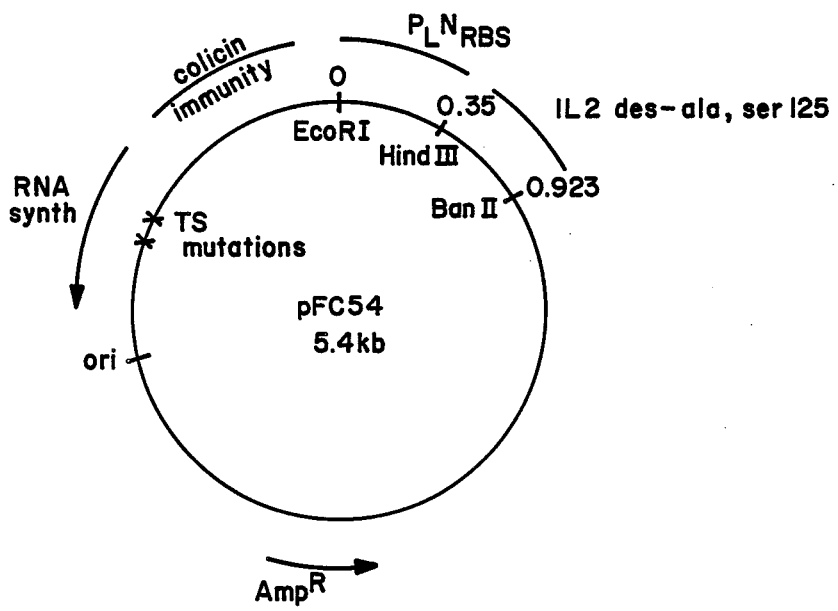
FIG._9.

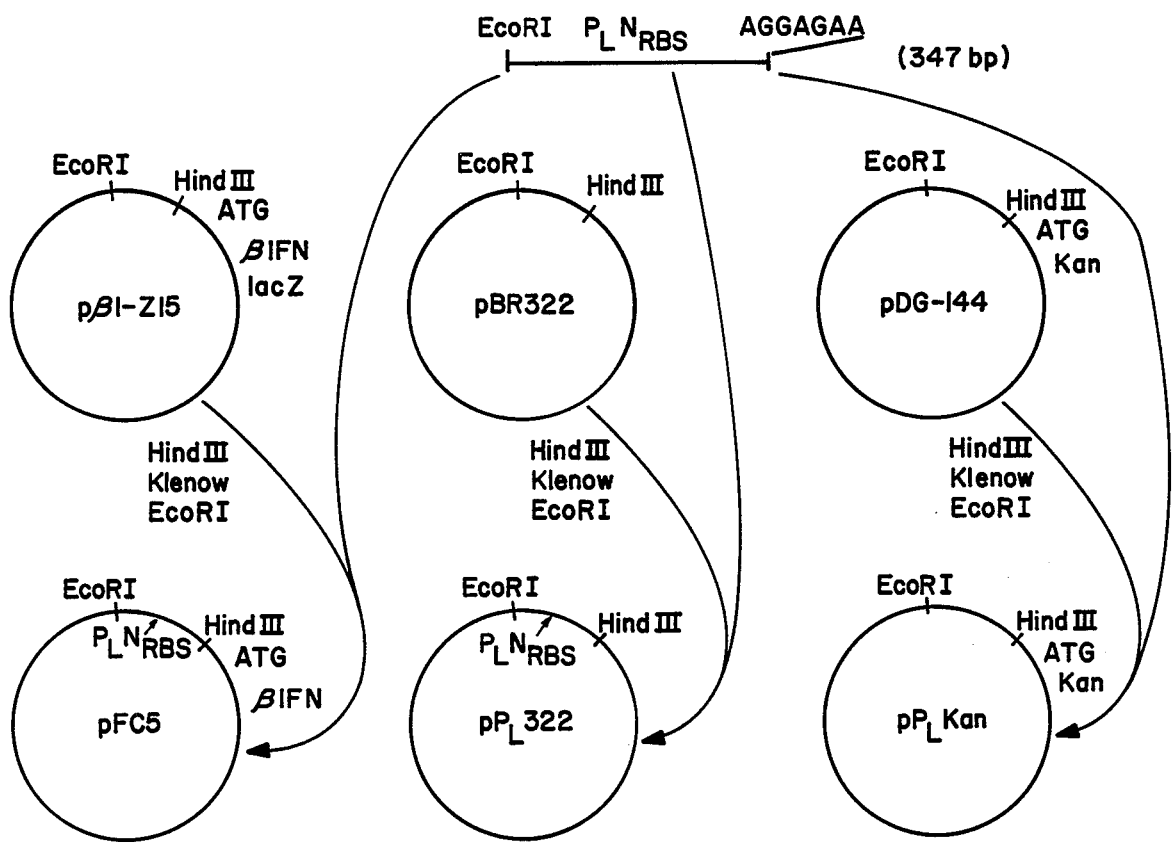
FIG._2.
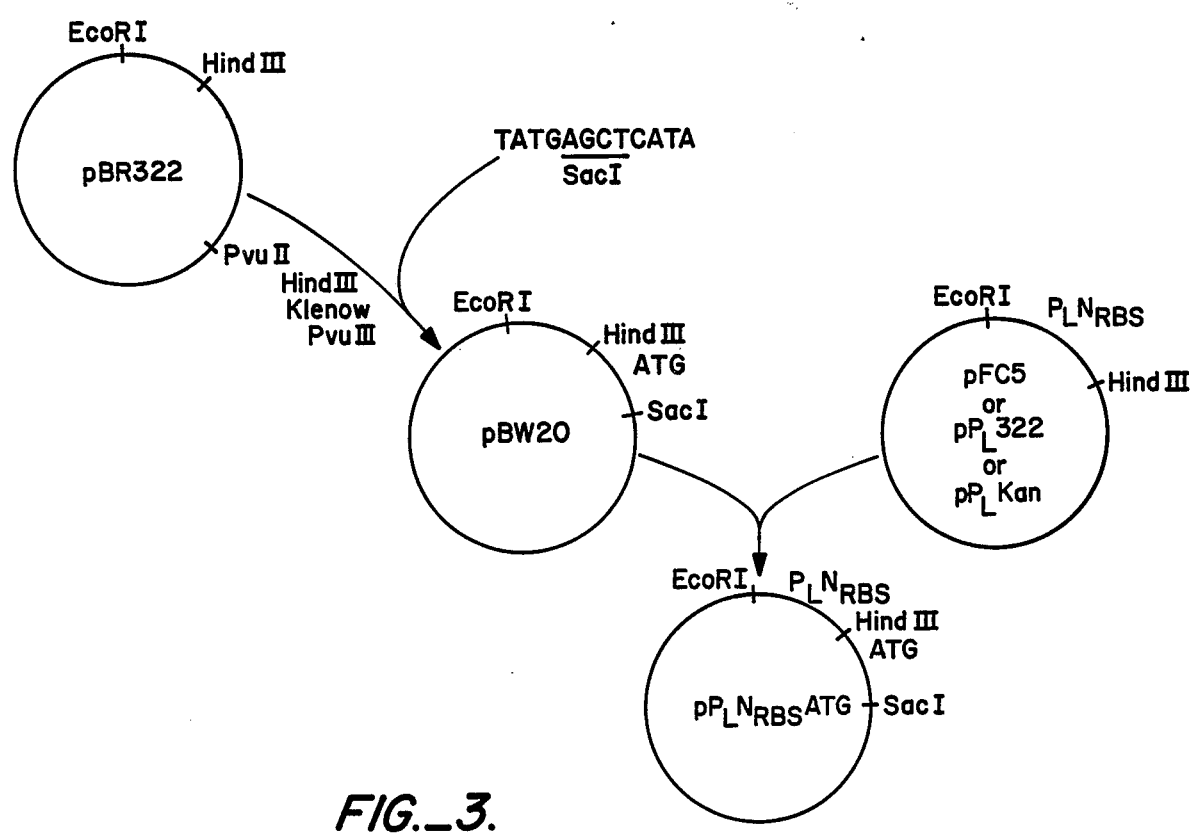
FIG._3.

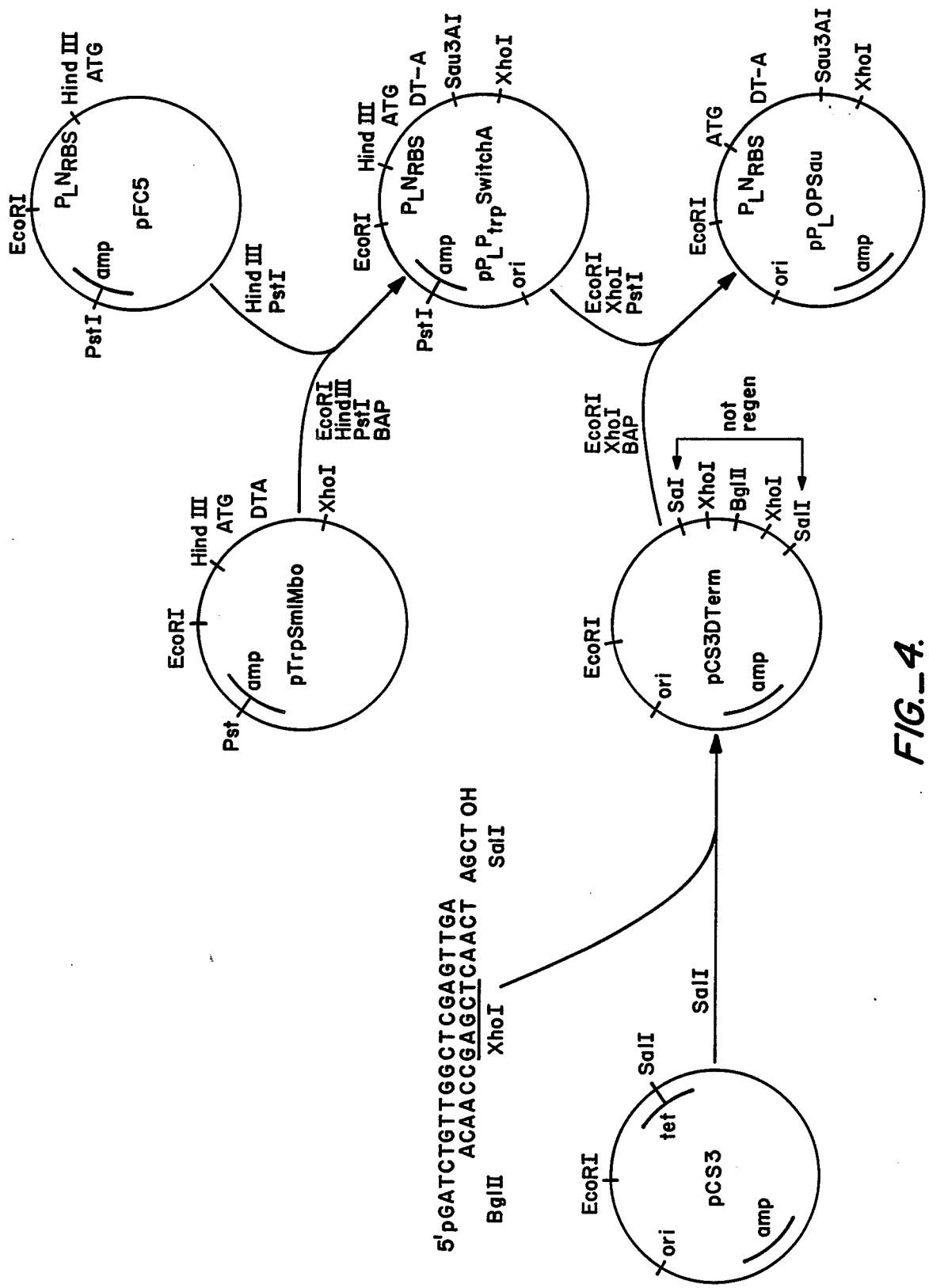
FIG._4.

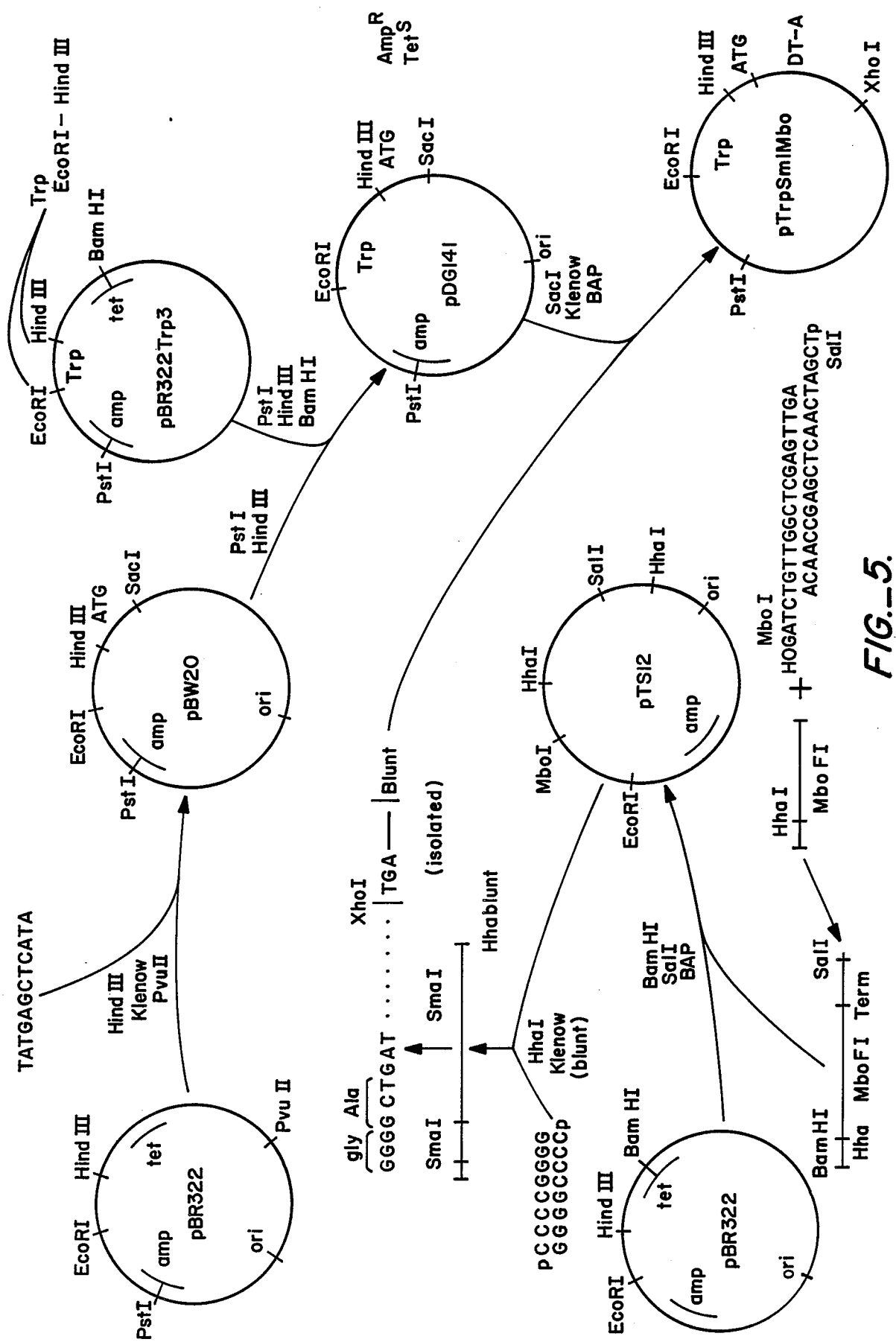
FIG._5.

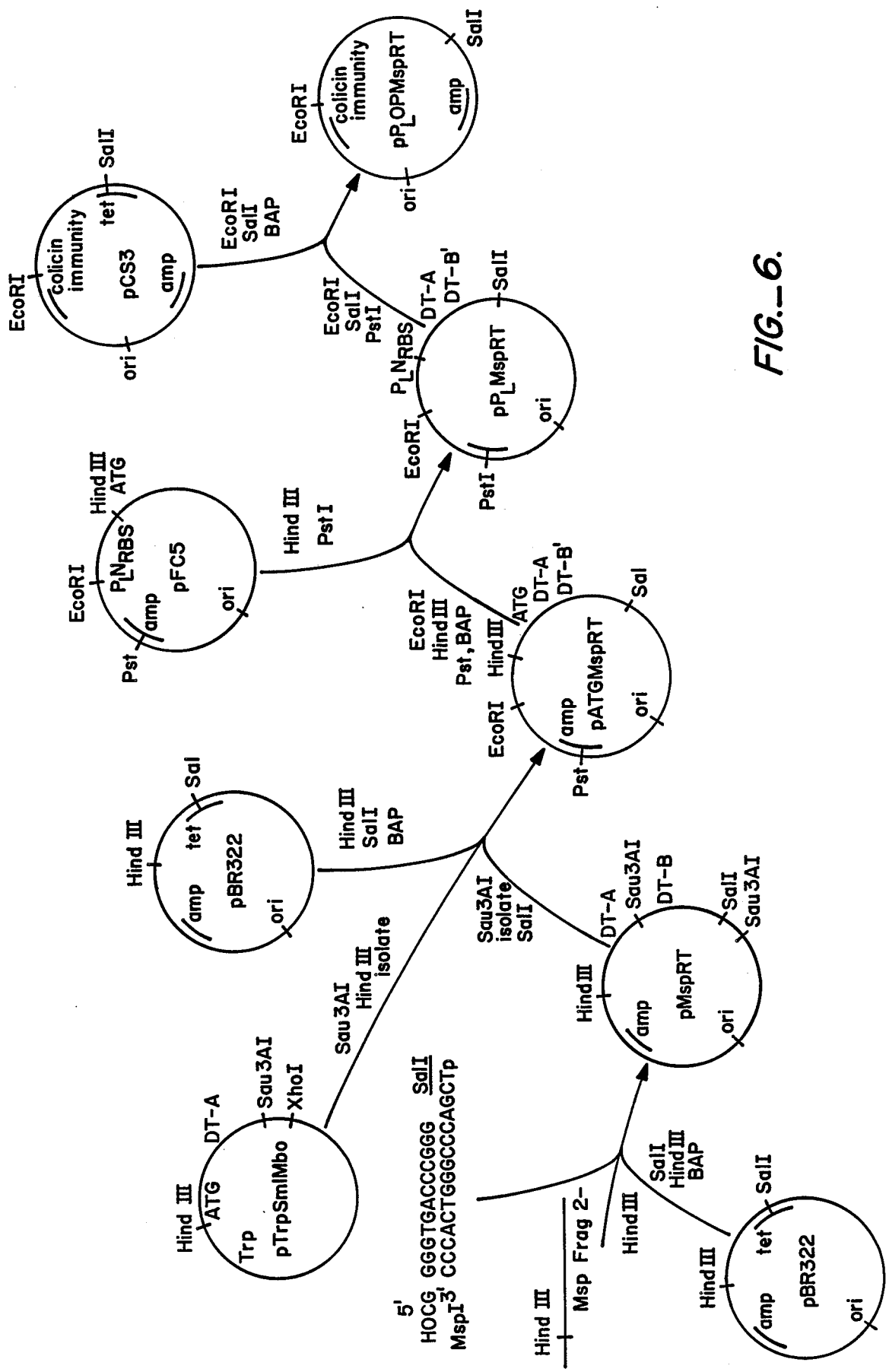
FIG._6.

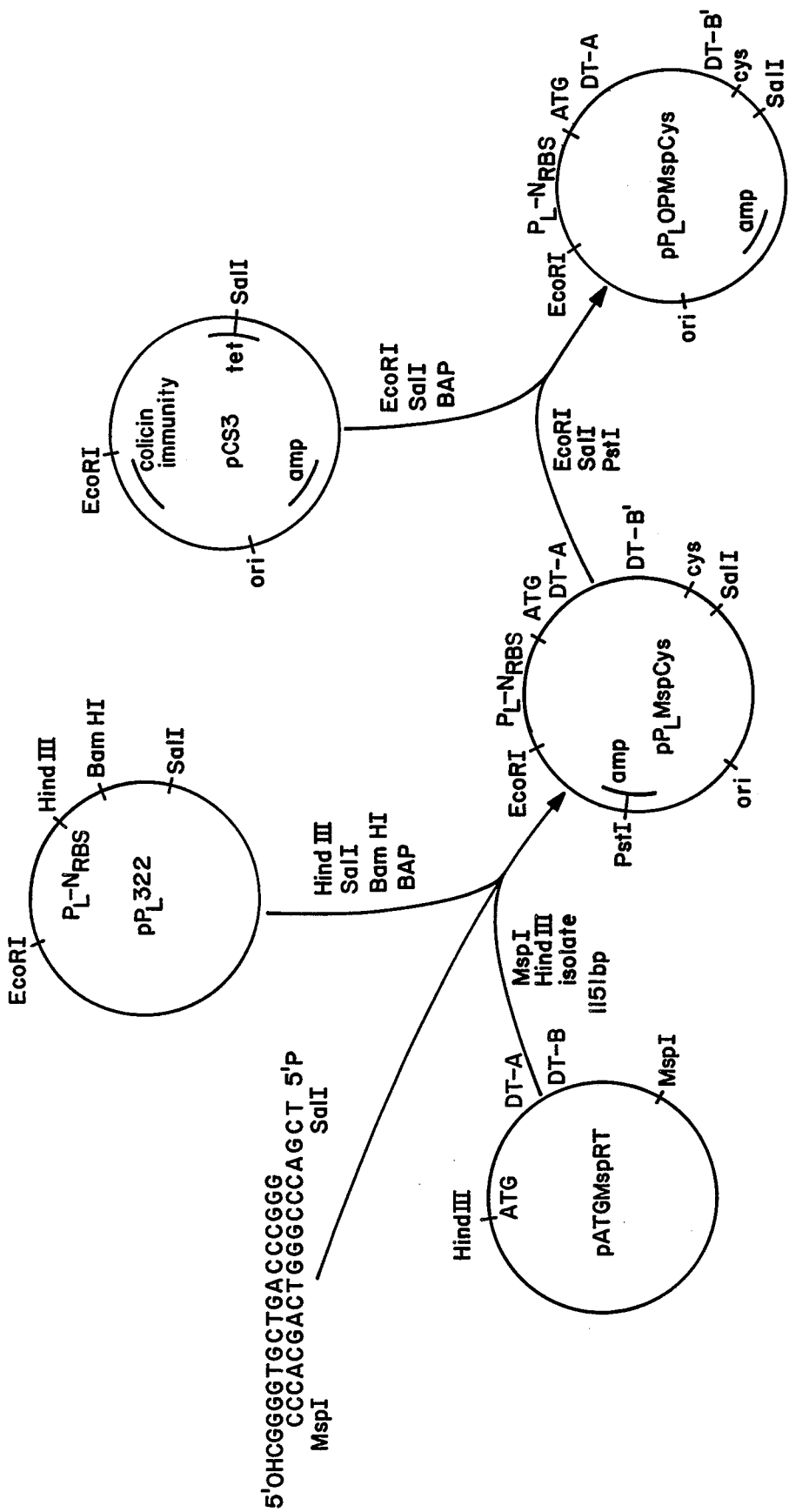
FIG._7.

PORTABLE TEMPERATURE-SENSITIVE CONTROL CASSETTE

CROSS-REFERENCE TO RELATED APPLICATIONS

This is a continuation-in-part of U.S. Ser. No. 646,693, filed 31 Aug. 1984, which in turn is a continuation-in-part of U.S. Ser. No. 578,133, filed 8 Feb. 1984 both abandoned.

DESCRIPTION

1. Technical Field

The present invention relates to construction of expression vectors in recombinant DNA technology. More specifically, it relates to providing novel, regulatable, fungible control systems.

2. Background Art

It is now generally understood by practitioners of biotechnology that successful expression of a coding sequence for a desired protein requires the utilization of a control sequence compatible with the host in which the protein is to be produced. Procaryotic hosts, as a general rule, express coding sequences under the control of a promoter and, optionally, operator in a sequence immediately preceding the 5' end of the encoded RNA transcript. Subsequent translation of the transcript is dependent upon the position of a ribosome binding site within a relatively few base pairs (bp) 5' of the start codon for the desired protein. The ribosome binding site (RBS) must, of course, be encoded in the original DNA sequence which contains the promoter/(operator) and the protein encoding sequence. Thus, in order to obtain successful production of the desired protein, the control sequences preceding the protein encoding sequences should include both a promoter/(operator) and a ribosome binding site.

It would be convenient to provide this control sequence as a portable cassette which could be shuttled between plasmids to precede a protein encoding sequence at will. Such portable sequences are, in fact, known in the art. For example, the trp promoter/operator system, including its ribosome binding site and some leader sequence codons, has been described in detail (Goeddel, et al, *Nucleic Acids Res* (1980) 8: 4057).

In addition to the convenience of a portable system, however, it is also required that the control system be regulatable by control of external parameters. Because bacterial hosts are often called upon to produce proteins which are not endogenous, premature production of these proteins during the growth phase of the culture may have an adverse effect on the health of the host cells. In order to obtain healthy growth, as well as a good quantitative protein production, it may be necessary to repress the expression of the desired gene during the growth phase of the culture, and then to permit expression after the growth phase has been substantially completed.

The presently available portable promoter systems, while subject to such control, are imperfect in their degree of attainment. For example, the above-mentioned trp promoter is regulated in response to the presence or absence of tryptophan in the medium. The promoter is turned on in the absence of tryptophan, but repressed in its presence. Neither a complete "on" or "off" position is attainable with such a promoter, however. For most bacteria, the indigenous repressor gene does not provide sufficient repressor to interact completely with the desirable higher levels of promoter/coding sequence constructs present on multi-copy plasmids within the cell. Conversely, since many proteins, desired to be synthesized, themselves contain tryptophan, it is not possible to delete tryptophan entirely from the medium when they are to be produced. Even approximate control is troublesome as medium exchange is often required to change the tryptophan level sufficiently.

The λ phage promoter, $P_L$, however, is subject to more finely tuned and convenient control, because the repressor which binds to its operator sequence can be temperature sensitive. The $P_L$ operator is repressed at low temperature by repressor proteins such as cI857 which are synthesized by appropriate mutant host cells. However, at higher temperatures, this repressor protein is deactivated, and the promoter is switched on. Thus, simply by raising the temperature of the culture, the synthesis of the desired protein sequence can be turned on. The $P_L$ promoter in its native environment operates to synthesize, among other things, an "N-gene" protein whose translation is controlled by an $N_{RBS}$ ribosome binding site. In the phage, the N-gene is the first coding sequence in the polycistronic message under the control of the $P_L$ promoter. $P_L$ promoter alone, and $P_L$ promoter on a sequence with the $N_{RBS}$ (which is not functionally utilized) have, indeed, been used previously to control the expression of genes encoding *E. coli* or foreign proteins in bacterial systems. See Shimatake, et al, *Nature* (1981) 292: 128; Remaut, E., et al, *Nucleic Acids Res* (1983) 11: 4677; Remaut, E., et al, *Gene* (1983) 22: 103. However, this control system has not been packaged into a readily transposable segment which can be shuttled from one expression vector to another with ease. In fact, disclosures of the location of the $N_{RBS}$ sequence in *E. coli* lambda phage, and therefore the composition of the disclosed sequence, have been grossly in error (Scherer, G. F. E., et al, *Nucleic Acids Res* (1980) 8:3895 at p 3898). The present invention succeeds in packaging this exquisitely regulatable control sequence into a conveniently excised segment which can be utilized for the expression of any desired protein sequence in a procaryotic host either with or without an operably linked ATG start codon. This is done by operably linking the sequence using available restriction enzymes to the coding sequence for the desired peptide.

The control cassette can be placed in suitable source vectors so that it can be used either by placing the $P_L N_{RBS}$ sequences in front of an ATG start codon, or the $P_L N_{RBS}$ can bring with it a blunt 3' end ATG for ligation onto N-terminal blunt-ended coding sequence for regulated expression of desired homologous or heterologous proteins.

DISCLOSURE OF THE INVENTION

The present invention is a "cassette" DNA sequence having convenient restriction sites at both 5' and 3' ends to provide ready protability, and having control elements for protein synthesis which are easily regulated by simple manipulations. The sequence contains the $P_L$ promoter from λ phage as well as the $N_{RBS}$ (ribosome binding site for N-gene), immediately preceding a restriction site.

Thus, in one aspect, the invention relates to a DNA sequence comprising the $P_L$ promoter operably linked to the $N_{RBS}$ having a restriction cleavage site within 6 bp downstream of the $N_{RBS}$. The invention also relates to vectors containing the DNA sequence above described. The resulting vectors may, of course, no longer contain the restriction cleavage site. Cells or cell cultures transformed with such vectors and progeny thereof are also an aspect of the invention.

In another aspect, the invention relates to a DNA sequence comprising the $P_L$ promoter operably linked to the $N_{RBS}$ and to an ATG start codon, the sequence having a restriction site within 6 bp downstream of the ATG, to vectors containing this sequence and to cells or cell cultures transformed with such vectors.

In other aspects, the invention relates to a method for producing a desired protein in recombinant host cells which comprises culturing the above-mentioned transformants and recovering the protein produced. In other aspects, the invention is directed to a method of constructing expression vectors which comprises ligating the $P_L N_{RBS}$ cassettes of the invention into operable position with respect to the desired coding sequences.

BRIEF DESCRIPTION OF THE DRAWINGS

FIG. 1 shows the construction of an EcoRI/HinfI(-repair) sequence containing $P_L N_{RBS}$.

FIG. 2 shows the construction of EcoRI/HindIII $P_L N_{RBS}$ cassette in pFC5, pP$_L$322 and pP$_L$Kan.

FIG. 3 shows the construction of pP$_L$N$_{RBS}$ATG containing the P$_L$N$_{RBS}$ATG cassette.

FIG. 4 shows the construction of pP$_L$OPSau.

FIG. 5 shows the construction of pTrpSmlMbo.

FIG. 6 shows the construction of pP$_L$MspRT.

FIG. 7 shows the construction of pP$_L$MspCys.

FIG. 9 shows the construction of pFC54.

MODES OF CARRYING OUT THE INVENTION

A. Definitions

Figure 8:
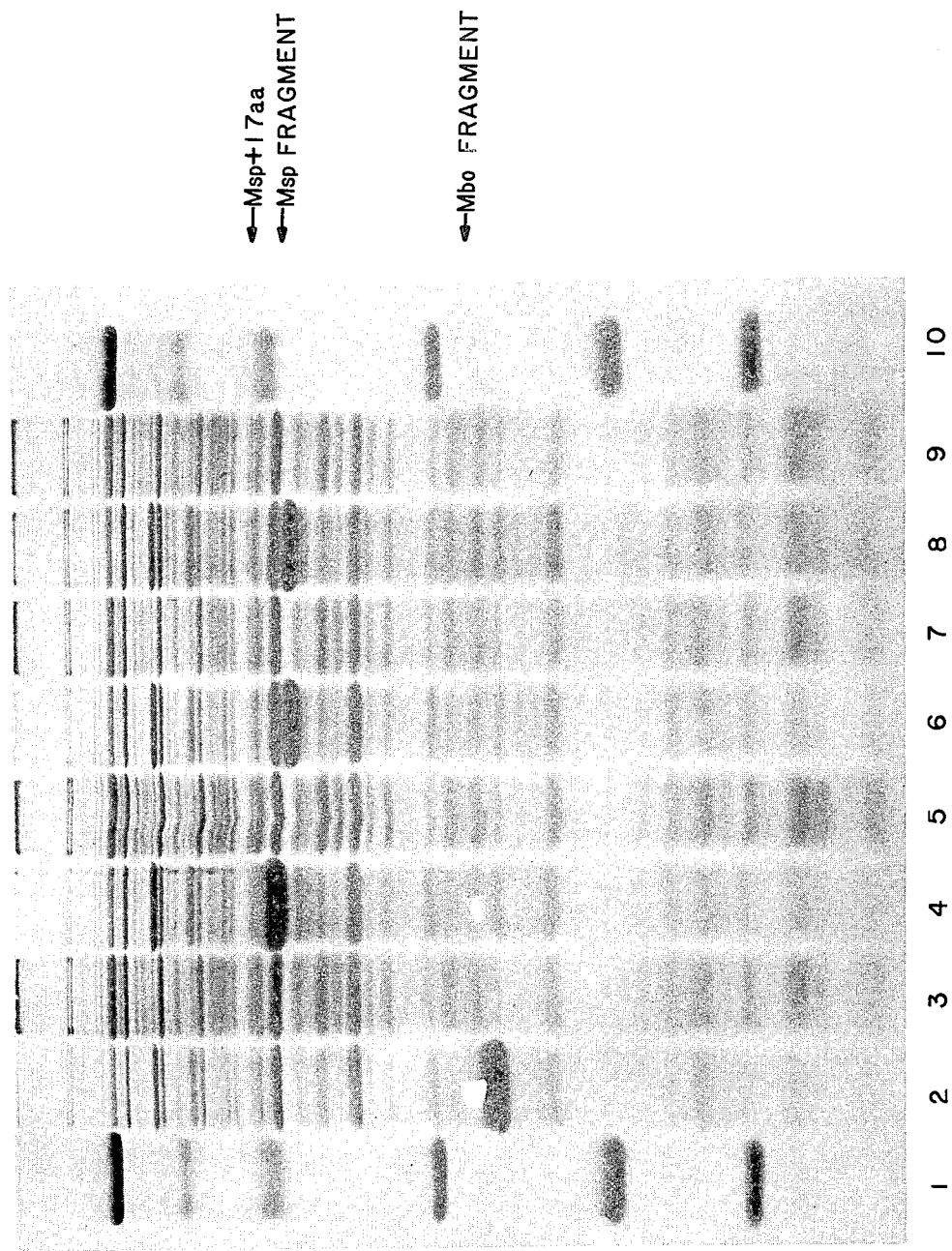
FIG. 8 gives the results of polyacrylamide gel electrophoresis on extracts of transformants.

"$P_L N_{RBS}$ cassette" refers to a DNA sequence which contains the $P_L$ promoter sequence operably linked to $N_{RBS}$, which cassette is bounded by restriction sites upstream of the $P_L$ promoter sequence and downstream from the $N_{RBS}$ sequence. While the exact location of the upstream restriction site is not of importance, the location of the downstream site must be close enough to permit operable juxtaposition to an ATG "start" codon. Thus, the downstream restriction site must permit cleavage within 6 bp of the last base pair of the RBS so that the entire cassette can be conveniently inserted within workable distance of an ATG start codon for the desired protein.

"$P_L N_{RBS}$ ATG-cassette" refers to a DNA sequence which contains a $P_L$ promoter operably linked to the $N_{RBS}$ coding sequence and to an ATG start codon. The cassette contains a downstream restriction site which permits cleavage within 6 bp 3' of the G of the ATG start codon. This permits convenient ligation of the blunted cassette into reading frame with a desired coding sequence.

Cleavage "within 'n' bp" of a given location requires that at least one of the two strands be so cleaved. As is known, most restriction enzymes catalyze cleavage in a jagged pattern, the cleavage site in one strand being separated by several bp from the cleavage site in the complementary strand. To fit the herein definition, only one of such sites needs to be within the required "n" bp.

The vectors containing the cassette of the invention may or may not contain a cleavage site as described above. Depending on the protocol for ligation of the cassette into a recipient vector, the site may or may not be lost.

"Operably linked" when used in regard to DNA sequence refers to the situation wherein the sequences are juxtaposed in such a manner so as to permit their ordinary functionality. For example, a promoter operably linked to a coding sequence refers to those linkages where the promoter is capable of controlling the expression of the sequence. The promoter operably linked to a ribosome binding site sequence has the same significance: ie, it permits the ribosome binding site to be positioned in the transcript so as to participate in the initiation of the translation of the RNA transcript. An RBS operably linked to a start codon is positioned so as to permit the start of translation at this codon.

"Recombinant host cell" refers to a cell which has been transformed with DNA sequences which have been manipulated by recombinant techniques.

"Cells" and "cell culture" are used interchangeably where the context so permits, and these terms include the progeny of any specific cells refined to. Thus, these terms refer to cells whether separated from or suspended in the medium and whether living or dead.

"$N_{RBS}$" and "$N_{RBS}$ corresponding sequence" or "ribosome binding site" and "ribosome binding site corresponding sequence" are also used interchangeably in that the embodiment intended will be clear from the context. Thus, when $N_{RBS}$ is used to describe a portion of DNA, clearly "$N_{RBS}$ corresponding sequence" is meant.

"IL-2" refers to proteins having sequence homology with, and the functionality of, interleukin-2. Proteins having the precise sequence of native IL-2 are included, as well as sequences containing sequence modifications which do not destroy activity. In the illustration set forth below, a modification or "mutein" having a serine residue rather than a cysteine at position 125 is used.

B. General Description

Three vector plasmids which are included in the invention, and which provide a convenient source for the $P_L N_{RBS}$ cassette containing a restriction site suitable for insertion of the cassette immediately upstream from an ATG are described. Other plasmids can easily be constructed by moving the cassette to any other host plasmids containing the proper sites. Such sites may be directly inserted into a host plasmid at the location of identical or compatible restriction sites normally available in the host plasmid, or at newly constructed compatible sites which can be engineered by digestion of the host plasmid at available sites and insertion of suitable commercially available linkers.

Additional plasmids are described which provide the $P_L N_{RBS}$-ATG cassette, i.e., the cassette contains the ATG start codon operably linked to the ribosome binding site. Other plasmids suitable for cloning this cassette can be constructed using methods known in the art.

The efficacy of the cassettes in terms of both portability and ease of regulation is shown hereinbelow by the production of diphtheria toxin fragments, and the construction of vectors for the expression of interleukin-2 (IL-2). Of course, any other suitable desired heterologous protein could be used. Further, while expression was demonstrated in specific strains of E. coli, which have been modified to encode the mutant $P_L$ repressor within their genomes, the vectors constructed containing the cassettes of the invention are effective in any procaryotic host which is capable of, or which has been capable of, synthesizing this mutant repressor. The specific examples that follow, thus, are illustrative rather than limiting. In these examples all temperatures are given in degrees Celsius.

C. Methods Employed

Isolation of the DNA fragments comprising the desired coding sequences is described in detail hereinbelow. Construction of suitable vectors containing the desired coding and control sequences employs standard ligation and restriction enzyme digestion techniques which are well understood in the art. Isolated plasmids, DNA sequences, or synthesized oligonucleotides are cleaved, tailored, and religated in the form desired.

The quantity of DNA available can be increased by cloning the desired fragments, i.e., inserting into a suitable cloning vehicle, such as pBR322, transforming and replicating in *E. coli*, and, optionally further enhancing through chlorampnenicol amplification or by phage replication. The desired fragments can then be removed from the cloning vectors or phage and ligated into other vectors as desired. Where vectors are to be used to express the gene for desired protein, suitable procaryotic hosts are transformed with the expression vectors and cultured under conditions which favor stabilization of the plasmid and the production of the desired protein. For the expression vectors of the invention, the conditions include repression of the controlling promoter until most of log phase has been completed by permitting growth at low temperature, and then an increase in temperature so as to favor the synthesis of the peptide.

When the peptide has been synthesized, the cells are lysed, and the desired peptide is recovered from the lysate by standard techniques. It is also within the scope of the invention, to include codons for a leader or signal sequence N-terminal to the desired peptide in the vector operably linked to cassettes of the invention. In such case, the peptide may be secreted into the medium or into the periplasmic space, depending on the host.

Site specific DNA cleavage is performed by treating with the suitable restriction enzyme (or enzymes) under conditions which are generally understood in the art, and the particulars of which are specified by the manufacturer of these commercially available restriction enzymes. See, e.g, New England Biolabs, Product Catalog. In general, about 1 $\mu$g of plasmid or DNA sequence is cleaved by one unit of enzyme in about 20 $\mu$l of buffer solution; in the examples herein, typically, an excess of restriction enzyme is used to insure complete digestion of the DNA substrate. Incubation times of about one hour to two hours at about 37° C. are workable, although variations can be tolerated. After each incubation, protein is heat inactivated, if applicable, or removed by extraction with phenol/chloroform and may be followed by ether extraction and the nucleic acid recovered from aqueous fractions by precipitation with ethanol optionally followed by running over a Sephadex G-50 spin column. If desired, size separation of the cleaved fragments may be performed by polyacrylamide gel electrophoresis using standard techniques. A general description of size separations is found in *Methods in Enzymology* (1980) 65: 499-560.

Restriction cleaved fragments may be blunt ended by treating with the large fragment of *E. coli* DNA polymerase I (Klenow) in the presence of the four nucleotide triphosphates (dNTPs) using incubation times of about 15 to 25 min at 20° to 25° C. in 50 mM Tris pH 7.6, 50 mM NaCl, 6 mM $MgCl_2$, 6 mM DTT and 0.1 mM dNTPs. The Klenow fragment fills in at 5' sticky ends but chews back single strands, even though the four dNTPs are present, at 3' sticky ends. If desired, selective repair can be performed by supplying only one of the, or selected, dNTPs within the limitations dictated by the nature of the sticky ends. After treatment with Klenow, the mixture is extracted with phenol/chloroform and ethanol precipitated followed by running over a Sephadex G-50 spin column. Treatment under appropriate conditions with S1 nuclease results in hydrolysis of any single-stranded portion.

Synthetic oligonucleotides are prepared by the triester method of Matteucci, et al (*J Am Chem Soc* (1981) 103: 3185-3191). Kinasing of single strands prior to annealing or for labeling is achieved using an excess, e.g., approximately 10 units of polynucleotide kinase to 1 nmole substrate in the presence of 50 mM Tris, pH 7.6, 10 mM $MgCl_2$, 5 mM dithiothreitol, 1-2 mM ATP, 1.7 pmoles $\gamma 32$ p ATP (2.9 mCi/mmole), 0.1 mM spermidine, 0.1 mM EDTA.

Ligations are performed using approximately equimolar amounts of the desired DNA fragments (2-10- $\times$ excess of linkers or small oligomers) suitably end tailored to provide correct matching, by treatment with an excess, i.e., in a typical 15-30 $\mu$l reaction 0.4-1 Weiss units $T_4$ DNA ligase. Ligation mixtures are buffered at approximately pH 7.6 using 66 mM Tris along with 5 mM magnesium ion, 5 mM dithiothreitol, 1 mM ATP, and 0.1 mg/ml BSA for either blunt-end or sticky end ligations. Incubations are carried out at approximately 14° to 25° C. overnight.

In vector construction employing "vector fragments," the vector fragment may be treated with bacterial alkaline phosphatase (BAP) in order to remove the 5' phosphate and prevent religation of the vector. BAP digestions are conducted at pH 8 in approximately 150 mM Tris, in the presence of $Na^+$ and $Mg^{+2}$ using about 1 unit of BAP per $\mu$g of vector at 60° for about one hour. In order to recover the nucleic acid fragments, the preparation is extracted with phenol/chloroform and ethanol precipitated and desalted by application to a Sephadex G-50 spin column. Alternatively, religation can be prevented in vectors which have been double digested by additional restriction of the unwanted fragments.

In the constructions set forth below, correct ligations for plasmid construction are confirmed by transforming *E. coli* strain MM294 obtained from *E. coli* Genetic Stock Center, CGSC #6135, or other suitable host with the ligation mixture. Successful transformants are selected by ampicillin, tetracycline or other antibiotic resistance or using other markers depending on the mode of plasmid construction, as is understood in the art. Plasmids from the transformants are then prepared according to the method of Clewell, D. B., et al, *Proc Natl Acad Sci* (1969) 62: 1159, following chloramphenicol amplification (Clewell, D. B., *J Bacteriol* (1972) 110: 667) and analyzed by restriction and/or sequenced by the method of Messing, et al, *Nucleic Acids Res* (1981) 9: 309, or by the method of Maxam, et al, *Methods in Enzymology* (1980) 65: 499.

Transformations in the examples below were performed using the calcium chloride method described by Cohen, S. N., et al, *Proc Natl Acad Sci* (USA) (1972) 69: 2110.

Two host strains were used in cloning and expression of the plasmids set forth below:

For cloning and sequencing, and for expression of some constructions, E. coli strain MM294 (supra), Talmadge, K., et al, Gene (1980) 12: 235; Meselson, M., et al, Nature (1968) 217: 1110, was used as the host. However, when expression is under control of the $P_L$ promoter and $N_{RBS}$ in the cassettes of the invention, the E. coli strain MC1000 or E. coli strain DG95, both lambda $N_7N_{53}cI857SusP_{80}$ lysogen were used as expression hosts. (The Lambda lysogen MC1000 derived strain is ATCC 39531 deposited Dec. 21, 1983. This strain is hereinafter sometimes referred to as MC1000-39531. The lambda lysogen DG95 strain, carrying pFC54, was deposited with the ATCC Sept. 4, 1984 and was given accession number 39831.) These strains contain lambda prophage which encodes a temperature sensitive cI repressor, which at the low temperature (30°–32° C.) is active. However, at the high temperature (36°–42° C.), the repressor is inactive and transcription from the $P_L$ promoter can proceed. It is further characteristic of these strains that at elevated temperatures the prophage fails to induce.

D. Construction of Plasmids with a Portable $P_LN_{RBS}$ EcoRI/HindIII Pre-ATG Cassette Three plasmids which serve as source of this cassette were prepared: pFC5, $pP_L322$, and $pP_LKan$.

D.1 Preparation of a $P_LN_{RBS}$ Fragment: 5'-EcoRI/-HinfI(repair)-3'

For each of these plasmids, the DNA sequence containing the $P_L$ λ phage promoter and the ribosome binding site for the N-gene ($N_{RBS}$) is obtained from a derivative of pKC30 described by Shimatake and Rosenberg, Nature (1981) 292: 128. pKC30 contains a 2.34 kb fragment from λ phage cloned into the HindIII/BamHI vector fragment from pBR322. The $P_L$ promoter and $N_{RBS}$ occupy a segment in pKC30 between a BglII and HpaI site. The derivative has the BglII site converted to an EcoRI site.

The BglII site immediately preceding the $P_L$ promoter was converted into an EcoRI site as follows: pKC30 was digested with BglII, repaired with Klenow and dNTPs, and ligated with T4 ligase to an EcoRI linker (available from New England Biolabs) and transformed into E. coli strain MM294 Lambda+. Plasmids were isolated from $Amp^R Tet^S$ transformants and the desired sequence was confirmed by restriction enzyme analysis. The resulting plasmid, pFC3, was double-digested with PvuI and HpaI to obtain an approximately 540 bp fragment framing the desired sequence. This fragment was partially digested with HinfI and the 424 bp fragment isolated and treated with Klenow and dATP, followed by SI nuclease, to generate a blunt-ended fragment with 3' terminal sequence -AG-GAGAA where the -AGGAGA portion is the $N_{RBS}$. This fragment was treated with EcoRI to give a 347 base pair DNA fragment with 5'-EcoRI/HinfI(partial repair, S1 blunt)-3' termini.

To obtain plasmids containing desired EcoRI/HindIII cassette containing $P_LN_{RBS}$, the resulting fragment was ligated into an EcoRI/HindIII(repaired) cleaved plasmid vector fragment obtained from one of three host plasmids: pβI-Z15, pBR322, or pDG144.

D.2 Preparation of pFC5 pβI-Z15, deposited 13 Jan. 1984, ATCC No. 39578, was prepared by fusing a sequence containing ATG plus 140 bp of β-IFN fused to lac-Z into pBR322. In pβI-Z15, the EcoRI site of pBR322 is retained, and the insert contains a HindIII site immediately preceding the ATG start codon. pβI-Z15 was restricted with HindIII, repaired with Klenow and dNTPs, and then digested with EcoRI. The resulting EcoRI/HindIII(repaired) vector fragment was ligated with the EcoRI/HinfI(-repaired) fragment above. The ligation mixture was used to transform MC1000-39531 and $Amp^R$ transformants containing the successful construction were identified by ability to grow on lactose minimal plates at 34° C. but not at 30° C. (Transformations were plated on X-gal-Amp plates at 30° C. and 34° C. and on minimal-lactose plates at 30° C. and 34° C. Transformants with the proper construction are blue on X-gal-Amp plates at both temperatures, but grow on minimal lactose plates only at 34°.) The successful construct was designated pFC5 and is diagrammed in FIG. 3.

D.3 Preparation of $pP_L322$

In the alternative, pBR322 may also be used as the cloning vector to carry the desired EcoRI/HindIII $P_L$-$N_{RBS}$ cassette. pBR322 was digested with HindIII, repaired with Klenow and dNTPs, and then further digested with EcoRI. The vector fragment was then ligated to the EcoRI/HinfI (repaired) fragment prepared above, and the ligation mixture transformed into MC1000-39531. Successful transformants were identified as $Amp^RTet^S$ at 30° C. but $Amp^RTet^R$ at 34° C. Plasmids were isolated from successful transformants and a successful ligation was confirmed by sequencing, and designated $pP_L322$.

D.4 Preparation of $pP_5Kan$

The third host plasmid vector used to obtain the cassette was pDG144, deposited 13 Jan. 1984, ATCC No. 39579. pDG144 is extensively described in another application and is not part of this invention. It is an altered pBR322 containing an intact $Amp^R$ gene, and a coding sequence for a protein conferring resistance to kanamycin ($Kan^R$). The $Kan^R$ coding sequence is preceded by a synthetic polylinker. Since pDG144 contains neither a promoter nor a ribosome binding site preceding the coding sequence, $Kan^R$ is not expressed, and cells harboring pDG144 are sensitive to kanamycin and to structurally similar antibiotics. The polylinker sequence immediately preceding the ATG start codon for the kanamycin gene can be removed by digesting with EcoRI and HindIII and $P_LN_{RBS}$ inserted.

Accordingly, pDG144 was digested with HindIII, blunt-ended with Klenow and dNTPs, and then digested with EcoRI. The vector fragment was ligated with the above-prepared EcoRI/HinfI (repaired) fragment and transformed into MC1000-39531. $Amp^R Kan^R$ colonies were selected, plasmids isolated and the correct sequence construction was verified by restriction analysis and sequencing. One plasmid containing the correct sequence was designated $pP_LKan$.

Each of the above resulting vectors, pFC5, $pP_L322$, and $pP_LKan$, may be used to clone and provide a source for the EcoRI/HindIII $P_LN_{RBS}$ cassette. The cassette can then conveniently be placed behind an ATG start codon which contains a HindIII site proximately preceding it.

E. Construction of Vectors Providing the $P_LN_{RBS}$-ATG Cassette-$pP_LN_{RBS}$ ATG and pDG141($P_L$)

The $P_LN_{RBS}$ cassette may also be provided with an operably linked ATG start codon by ligation of the des-ATG cassette into a suitable host vector. pBW20, a derivative of pBR322 containing a synthetic sequence providing an ATG start codon an appropriate distance downstream from a HindIII site, can be thus used.

To prepare pBW20, pBR322 was digested with HindIII, repaired with Klenow and the four dNTPs, then digested with PvuII. The vector fragment was then ligated in a standard blunt-end ligation with the self-complementary dodecamer TATGAGCTCATA, which contains a SacI recognition site partially overlapping and downstream from the ATG sequence. The ligation mixture was transformed into *E. coli* MM294, and correct construction confirmed by isolation of the plasmids and Maxam Gilbert sequencing. The resulting pertinent sequence in pBW20 is as follows:

```
      HindIII            SacI
 ----A A G C T T A T G A G C T C A T A C T G----
      pBR322      |                      pBR322
```

To prepare pP$_L$N$_{RBS}$ ATG, any one of pFC5, pP$_L$322, or pP$_L$Kan is digested with HindIII and EcoRI and ligated to the EcoRI/HindIII digested BAPed vector fragment from pBW20, transformed into *E. coli* MC1000-39531. Amp$^R$ colonies were selected, and the desired vector construction was confirmed by sequencing or restriction enzyme analysis.

One cloned colony containing the correct construction, pP$_L$N$_{RBS}$ ATG, thus provides a source for a P$_L$N$_{RBS}$-ATG cassette in a host plasmid suitable for insertion of a gene sequence desired to be expressed. The properly restricted host vector containing the cassette can be provided by digestion with SacI, blunt ending with Klenow or SI nuclease, and insertion of the blunt-ended gene.

pDG141, deposited in the ATCC on 24 Jan. 1984, and given accession number 39588, can also provide the ATG for the P$_L$N$_{RBS}$-ATG cassette. pDG141 contains the same dodecamer insert as pBW20 in front of a trp promoter cassette. Thus, following the procedure of the previous paragraph, but substituting for pBW20, pDG141, the analogous plasmid pDG141(P$_L$) is obtained.

F. Use of the P$_L$N$_{RBS}$ Cassette in Expression

The following examples illustrate one aspect of the invention by describing the construction of expression vectors suitable for production of certain diphtheria toxin fragments, and of IL-2 and the successful expression of the appropriate coding sequences. The diphtheria toxin fragments produced are useful in construction of conjugate immunotoxins. IL-2 and its modified forms are members of a class of proteins designated lymphokines which are useful in therapy directed against deviant cell metabolism. Of course, any desired peptide could be analogously produced by providing the appropriate coding sequence in a manner analogous to that illustrated for production of diphtheria toxins and of IL-2. Further, rather than the P$_L$N$_{RBS}$ cassette, the P$_L$N$_{RBS}$ ATG cassette could be placed in front of the codons for the desired peptide as described above.

G. Expression of DT Fragments

The construction of three pBR322-based plasmids modified to effect the production of particular diphtheria toxin fragments is illustrated below. These vectors are pP$_L$P$_{trp}$ Switch A, an expression vector for production of a portion of diphtheria toxin which encodes the "A" portion (DT-A), and pP$_L$MspRT, and pP$_L$MspCys, which encode a protein sequence representing the A fragment and a portion of the B fragment of diphtheria toxin (DT-A-B'). Each of the foregoing can be further modified to convert it to a high copy number plasmid thus providing pP$_L$OPSau, pP$_L$OPMspRT, and pP$_L$OPMspCys, respectively, for expression of the designated DT-A and DT-A-B' fragments at still higher levels. The high copy number plasmids provide an additional mechanism for production of increased amounts of protein—elevation of the temperature at which the culture is maintained results not only in switching on the P$_L$ promoter, but also in increasing the copy number of the appropriate plasmid, thus achieving a substantial elevation in the amount of protein produced.

The nature of the DT-A and DT-A-B' fragments is described in detail in a copending application; production of these fragments per se does not constitute part of this invention, but merely is illustrative of the efficacy of the portable P$_L$-N$_{RBS}$ cassette.

Briefly, for clarity, the DT-A fragment corresponds roughly to a segment of the diphtheria toxin which is encoded by a DNA sequence isolated by MboI digestion of the toxin gene sequence. DT-A contains approximately the first 200 amino acids of the toxin. The DT-A-B' fragment corresponds to a protein sequence encoded by a DNA fragment isolated similarly using MspI; it contains slightly less than 400 of the N-terminal amino acids of the toxin. The "Msp fragment" used in obtaining expression of DT-A-B' and the "Mbo fragment" used in obtaining expression of DT-A were prepared as set forth below.

G.1 DT Fragment Coding Sequence Isolation

DNA was isolated from corynephage $\beta^{Tox+}$ grown in *Corynebacterium diphtheriae* C7(−)tox−. (The host and phage are obtainable from J. Collier, University of California, Los Angeles: Tweten, R. K., et al, *J Bacteriol* (1983) 156: 680.)

To prepare DNA, high-titered β phage stocks were prepared in "TYE' medium" (15 g/l bactotryptone, 10 g/l yeast extract 5 g/l NaCl supplemented with 1 mM CaCl$_2$) by the method of Holmes, R. K., et al, *J. Virology* (1969) 38: 586. Upon completion of lysis, debris was removed by centrifugation at 13,000× g for 5 min, and NaCl added to 0.5M, followed by PEG to 100 g/l, and the mixture was stirred overnight at 4° C. The phage were concentrated by centrifugation at 13,000×g for 15 min and resuspended in 100 mM Tris HCl pH 7.5, 100 mM NaCl, 20 mM EDTA. Pronase was added to 1 mg/ml and the mixture was incubated at 37° C. for 2 hr. After removal of PEG by addition of potassium phosphate (⅔ dibasic, ⅓ monobasic) to 23% and centrifugation at 6,000×g for 5 min, the lower phase was extracted with phenol/chloroform, ethanol precipitated and the DNA purified by banding in a CsCl-EtBr gradient.

Approximately 500 μg of the phage DNA (MW=22×10$^6$ daltons) were treated with EcoRI and XbaI and the resulting mixture run on a 1.7 liter 1% agarose gel at 90 volts for 35 hr. The XbaI/EcoRI (fragment 1.5×10$^6$ daltons) containing the toxin gene was cut out, run through a syringe, and electroeluted in 1/10 TBE for 4 hrs at 500 volts onto a spectropore dialysis membrane. The DNA was retrieved from the membrane using 0.25% SDS in 1/10 TBE, phenol extracted, ether extracted, and ethanol precipitated.

To prepare and clone the "Msp fragment," the resulting DNA was further restricted with MspI, the DNA resolved on 5% PAGE, and the two MspI fragments obtained were isolated by the crush and soak method. The large Msp fragment, which contained control sequences, leader, A, and partial B (B') sequences from the toxin, was cloned by ligating approximately 5 ng of the fragment with 2 µg of ClaI-restricted, BAPed, pBR322. The ligation mixture was transformed into *E. coli* MM294, and the desired clones were determined by isolation of plasmids, restriction analysis and sequencing. The desired recombinant plasmid was designated pMsp.

The "Mbo fragment" was prepared and cloned in an analogous manner except that MboI was used for restriction, and the resulting 831 bp fragment isolated and cloned into pBR322 which had been BamHI restricted and BAPed. The desired recombinant plasmid was designated pMbo.

Although the desired fragments were thus cloned, construction of expression vectors as described below generally employed Msp or Mbo fragments isolated directly from phage as described above.

G.2 pP$_L$OPSau (Expression Vector for DT-A)

The construction is outlined in FIG. 4.

To provide a properly terminated DT-A fragment, the synthetic oligonucleotide

| | | | | | | |
|---|---|---|---|---|---|---|
| GA | TCT | GTT | GGC | TCG | AGT | TGA |
| Arg | Ser | Val | Gly | Ser | Ser | Term | which encodes the six amino acids normally found sequential to the Arg at position 193 of native DT and a stop codon, was kinased and annealed to a complementary sequence to give the double stranded sequence:

```
                  XhoI
5'-P— GATCTGTTGGCTCGAGTTGA
              ACAACCGAGCTCAACTAGCT —5'.
BglII                              SalI
```

The fragment has a phosphorylated BglII site and a nonphosphorylated SalI site. This fragment was ligated with SalI digested pCS3 (see para. F.5) to obtain pCS3DTerm which results from ligation of an inverted duplication of the synthetic oligonucleotides (formed by annealing the BglII ends of two of the synthetic oligonucleotides) to insert a symmetrically duplicated termination sequence pair. The vector fragment from EcoRI/XhoI digestion of pCS3DTerm (see FIG. 4) thus provides that portion of the termination sequence downstream from the XhoI site. The thus digested BAPed vector from pDC3DTerm was ligated with a fragment containing the $P_LN_{RBS}$ cassette operably linked to the DT-A fragment and the upstream XhoI portion of the termination sequence. This latter fragment is obtained by EcoRI/XhoI (PstI to prevent religation) digestion of $P_LP_{TRP}$ Switch A (see below). The resulting plasmid, $pP_LOPSau$, includes the $P_LN_{RBS}$ sequence immediately preceding the ATG start codon for DT-A linked to mature protein encoding sequence of the MboI DNA fragment with its terminator.

G.2.a $P_LP_{trp}$ Switch A $P_LP_{trp}$ Switch A is prepared from $P_{Trp}$SmlMbo (see below) and pFC5 (see para. D.2) as follows (see FIG. 4).

55 μg pTrpSmlMbo was treated with EcoRI, HindIII and PstI, and the vector portion treated with BAP. 5 μg of the vector fragment was ligated to 5 μg of HindIII/PstI digested pFC5. 0.3 μg of the ligation mixture DNA was transformed into MC1000-39531 cells, $Amp^R$ clones were selected and the desired construction confirmed by restriction was analysis, and designated $pP_LP_{Trp}$ Switch A. (Growth of these transformants on TYE′ medium containing 100 μg/ml ampicillin at 30° for 7 hr, followed by heating to 60° C. to raise quickly the medium temperature to 42° and growth at 42° C. for 1 hr resulted in production of DT-A at a concentration of 5–20 μg/ml as assayed by the procedure of Chung & Collier, *Infect Immun* (1977) 16:832.)

G.2.b pTrpSMlMbo pTrpSmlMbo contains the DT-A fragment coding sequence followed by the Mbo terminator sequence (supra) under the control of the trp promoter. The construction is from pTS12 (a plasmid containing the DT-A and Mbo terminator) and pDG141, which contains the trp promoter (see FIG. 5).

53.5 μg of pTS12 was digested with HhaI, blunt-ended with Klenow, and 18 μg of the resultant fragments ligated to 3.15 nmoles of phosphorylated oligomeric linker CCCCGGGG, and then treated with SmaI. The resulting sequence at the 5′ terminus was thus modified to give the sequence GGGGCTGA which encodes the peptide sequence beginning with amino acid 1 of the DT-A fragment (see FIG. 5). The 3′ end of the ligation product terminates in the first HhaI site of pBR322 following the SalI site, and the fragment contains the entire DT-A coding sequence in reading frame with terminator for the small Mbo fragment. The desired 654 bp fragment was then isolated following 6% polyacrylamide gel electrophoresis using the crush and soak method.

One picomole of this modified prepared fragment was ligated with 0.7 μg (0.04 pmoles) of pDG141 which had been restricted with SacI, blunt-ended with Klenow, and BAPed (the preparation of pDG141 is described below). The pDG141-derived fragment has an ATG start codon operably linked to the trp promoter. The resulting ligation mixture was transformed into *E. coli* MM294, and resistant colonies were grown in 10 ml TYE′ medium containing 100 μg/ml ampicillin and screened for plasmid size. Those colonies which contained plasmids larger than pDG141 were screened for expression of the DT-A fragment. The cells were grown to log phase in 10 ml TYE′ medium containing 100 μg/ml ampicillin at 37° C. for 4 hr. 1 ml of cells was centrifuged and the pellet resuspended in 20 μl of buffer containing 62.5 mM Tris pH 6.8 3% SDS. Following heating at 95° C. for 5 min, the samples were run on a 12.5% SDS polyacrylamide 3% stacking gel according to Laemmli (*Nature* (1970) 227: 680). Two clones which showed an additional protein band at the expected molecular weight were confirmed by measuring the EF-2 ADP-ribosylation activity, according to the procedure of Chung, D. W., et al, *Infect Immun* (1977) 16: 832. These colonies, designated pTrpSmlMbo, produced 20 μg of DT-A per ml culture. The molecular weight and antigenicity of the product were confirmed by Western Blot.

G.2.c Preparation of pDG141 pDG141 contains the trp control sequences immediately upstream from an ATG start codon. It was deposited with the ATCC 24 Jan. 1984, and given the accession number 39588. The sequence downstream of the ATG provides a SacI cleavage site which cuts 3′ between the T and the succeeding bp. In the construction of pDG141, a derivative of pBR322 is used to provide a trp (PstI/HindIII) cassette and pBW20 to provide the ATG and SacI site.

12 ng of pBR322-Trp3 restricted with PstI and HindIII was ligated with 1.34 ng of similarly restricted pBW20. The ligation mixture was subsequently digested with BamHI to linearize any ligation products which contained the HindIII/PstI unwanted vector fragment from pBR322-Trp3. The ligation mixture was used to transform *E. coli* MM294, and the desired colonies were selected on plates of L-Broth containing 50 μg/ml ampicillin pre-spread with 500 μg tryptophan. Correct construction was confirmed by sequencing.

G.2.c.1 Preparation of pBR322-trp3

The trp promoter/operator/ribosome binding site sequence, lacking the attenuator region, was obtained from pVH153, supplied by C. Yanofsky, Stanford University. Trp sequences are available in a variety of such plasmids known in the art. pVH153 was treated with HhaI (which cuts leaving an exposed 3' sticky end just 5' of the trp promoter) blunt-ended with Klenow, and partially digested with TaqI. The 99 bp fragment corresponding to restriction at the TaqI site, 6 nucleotides preceding the ATG start codon of the trp leader protein was isolated, and then ligated to EcoRI(repair)/ClaI digested pBR322 to provide pBR322-Trp 3. The aforementioned TaqI site encodes a 5' half ClaI site, hence ligation to a 3' half ClaI site (from pBR322) will regenerate a functional ClaI site. Additionally, the HindIII site immediately downstream from the pBR322 ClaI site permits excision of the desired trp fragment as an EcoRI/HindIII cassette.

G.2.c.2 Construction of pBW20 pBW20 contains a synthetic ATG-containing dodecamer cloned into the HindIII/PvuII vector fragment from pBR322. The dodecamer, TATGAGCTCATA, contains SstI (or SacI) sites.

pBR322 was digested with HindIII, repaired with Klenow and the four dNTPs, and then digested with PvuII. The vector fragment was ligated with the self-complementary dodecamer and transformed into *E. coli* MM294 and the correct construction confirmed by plasmid isolation and sequencing.

G.2.d pTS12

The oligonucleotide

```
GA  TCT  GTT  GGC  TCG  AGT  TGA
    Arg  Ser  Val  Gly  Ser  Ser  Term
``` which encodes the amino acid sequence subsequent to the Mbo cleavage site for six additional amino acids prior to a termination codon was synthesized using the triester method of Matteucci, et al (supra); kinased and hybridized to the complementary synthetic fragment as described in paragraph F.2 in connection with pCS3DT synthesis. One pmole double-stranded oligonucleotide was placed in a three-way ligation mixture with 1.4 pmoles (0.8 μg) of Mbo fragment 1 and the vector fragment formed from 1 μg pBR322 which had been treated with BamHI, SalI and BAP. The mixture was ligated overnight before transforming into *E. coli* MM 294. $Amp^R Tet^S$ colonies were selected and the desired construction confirmed by DNA isolation restriction analysis and DNA sequencing. The desired plasmid was designated pTS12.

G.3 Preparation of pP$_L$OPMspRT pP$_L$OPMspRT is constructed as shown in FIG. 6. EcoRI, SalI digested/BAPped pCS3 (see para. E.4) was ligated to EcoRI/SalI (PstI to prevent religation) digested pP$_L$MspRT (see below). The resulting ligation mixture was transformed into MC1000-39531 and the $Amp^R Tet^S$ transformants were analyzed by restriction analysis to confirm the correct construction of pP$_L$OPMspRT which contains properly started and terminated DT-A-B' under the control of the P$_L$N$_{RBS}$ cassette.

G.3.a. Construction of pP$_L$MspRT

This plasmid derives from pATGMspRT as the source of the protein coding sequence with a properly placed start codon preceding the first amino acid of the native DT-A, and pFC5 as the source of the P$_L$N$_{RBS}$ cassette. It constructed by taking advantage of the portability of the P$_L$N$_{RBS}$ cassette. A PstI/HindIII digest of pFC5, was mixed with a PstI/HindIII (EcoRI to prevent religation) digest (BAPed) of pATGMspRT to give the desired pP$_L$MspRT. The ligation mixture was used to transform MC1000-39531 and $Amp^R$, $Tet^S$ colonies selected. Correct construction of pP$_L$MspRT was confirmed by plasmid isolation and restriction.

G.3.b Construction of pATGMspRT pATGMspRT contains the coding sequence for DT-A-B' (with the termination sequence) immediately preceded by the ATG start codon. It is constructed in a 3-way ligation from pTrpSmlMbo, pBR322, and pMspRT, as shown in FIG. 4 (pMspRT contains the Msp fragment and the synthetic terminator cloned into pBR322).

pTrpSmlMbo was restricted with Sau3AI and HindIII, and the 586 bp fragment containing the ATG start codon, A fragment codons and Mbo terminator isolated. (The Sau3AI site is immediately upstream of the XhoI sequence of the terminator.) pMspRT, used as a source of the B' fragment along with its terminator, was treated with Sau3AI, and the 750 bp fragment containing the above-mentioned portions isolated. This latter fragment was then restricted with SAlI. The two fragment preparations were then ligated into vector fragment from HindIII/SalI double digested, BAPed pBR322 and transformed into *E. coli* MM294 and the desired construction pATGMspRT was verified.

G.3.c Construction of pMspRT

The construction of this plasmid is also shown in FIG. G. An Msp fragment, isolated as in paragraph D, was digested with HindIII, and ligated into HindIII/SalI digested, BAPed vector fragment of pBR322 in a three-way ligation, along with kinased and annealed Msp terminator (synthetically derived as shown in FIG. 4). The ligation mixture was transformed into *E. coli* MM294, plasmids were isolated from $Amp^R Tet^S$ colonies, and the correct construction confirmed by sequencing.

G.4 Construction of pP$_L$OPMspCys

In order to provide a cysteine residue for use in linkage to form conjugate toxins, the DT-A-B' fragment was modified by adding a cysteine residue. In so doing, of course, the fragment maintains its DT-A-B' fragment status as set forth in the definition section above.

By providing a cysteine residue at the carboxy terminus, the DT-A-B' fragment is now capable of forming a thioether linkage wih a suitable reactive linker molecule which can, in turn, be covalently bound to a suitable antibody or antibody fragment to confer specificity on the DT-A-B' fragment. Suitable linker molecules which form thioether linkages at one end and ester linkages or amide linkages at the other include 6-maleimidocaproic acid, 2-bromoacetic acid, 2-iodoacetic acid, all of them in their acyl activated derivatized forms, such as the succinimidyl ester. The use of such linking agents is well understood in the art. The resulting conjugate will contain the enzymatically active portion of the diphtheria toxin fragment, the intracellularly cleavable/extracellularly stable junction normally found in DT between the A and B fragments, the sequence in DT-B believed responsible for the translocation function—i.e., facilitation of entry into the target cell, all covalently and stably bound through the linker to a target cell specific antibody moiety.

The construction contains the desired coding sequence under the control of $P_LN_{RBS}$ on a temperature sensitive high copy number plasmid analogous to the previous constructions for DT-A and DT-A-B' above. It is outlined in FIG. 7.

pCS3 was cleaved with EcoRI/SalI and BAPed to provide the vector fragment providing for high copy number. This vector fragment was ligated with $pP_L$MspCys (see below), which had been restricted with EcoRI, SalI (and PstI to prevent self ligation). Successful $Amp^RTet^S$ transformants into MC1000-39531 were isolated, and the desired construction was confirmed by plasmid isolation and restriction analysis. A successful construction was designated $pP_L$OPMspCys.

G.4.a Construction of $pP_L$MspCys

This construction is also outlined in FIG. 5. The vector fragment and the $pP_LN_{RBS}$ segments are provided by a HindIII/SalI (BamHI to prevent religation) restriction digest of $pP_L$322 (see paragraph E.5 below). The coding sequences for DT-A and the B' fragment up to the Msp restriction site are provided by a MspI/HindIII digest of pATGMspRT (see paragraph E.2.b above). The 1151 bp fragment is isolated from this double digest for ligation. The terminating sequences for the cys-containing construct are provided by the synthetic double-stranded oligonucleotide

```
5'HO CGGGGTGCTGACCCGGG
         CCCACGACTGGGCCCAGCT P—5'
     MspI                    SalI
``` shown in FIG. 5, which is an MspI-SalI fragment. These three fragments were ligated under standard conditions and the ligation mixture was used to transform MC1000-39531. Successful tranformants ($Amp^R$ $Tet^S$) were selected, plasmid DNA was isolated, and the correct construction, $P_L$MspCys, was confirmed by sequence analysis.

G.5 Construction of pCS3—A High Copy Number Plasmid

PCS3 provides the origin of replication to insure high copy number for all of the foregoing DT expression vectors. This plasmid was deposited with the ATCC on June 3, 1982, and given ATCC No. 39142. The construction of this plasmid is also described in EP 96,586, published Dec. 21, 1983.

pCS3 is derived from pEW27 and pOP9. pEW27 is described by E. M. Wong, *Proc Natl Acad Sci* (*USA*) (1982) 79:3570. It contains mutations near its origin of replication which provide for temperature regulation of copy number. As a result of these mutations replication occurs in high copy number at high temperatures, but at low copy number at lower temperatures.

pOP9 is a high copy number plasmid at all temperatures which was constructed by inserting into pBR322 the EcoRI/PvuII origin containing fragment from Col E1 type plasmid pOP6 (Gelfand, D., et al, *Proc Natl Acad Sci* (*USA*) (1978) 75: 5869). Before insertion, this fragment was modified as follows: 50 μg of pOP6 was digested to completion with 20 units each BamHI and SstI. In order to eliminate the SstI 3' protruding ends and "fill in" the BamHI 5' ends, the digested pOP6 DNA was treated with *E. coli* DNA polymerase I (Klenow) in a two-stage reaction first at 20° C. for elimination of the 3' SstI protruding end and then at 9° C. for repair at the 5' end. The blunt-ended fragment was ligated and 0.02 pmole used to transform competent DG75 (O'Farrell, P., et al, *J Bacteriology* (1978) 134: 645-654). Transformants were selected on L plates containing 50 μg/ml ampicillin and screened for a 3.3 kb deletion, loss of an SStI site, and presence of a newly formed BamHI site.

One candidate, designated pOP7, was chosen and the BamHI site deleted by digesting 25 μg of pOP7 with 20 units BamHI, repairing with *E. coli* DNA polymerase I fragment (Klenow), and religating with T4 DNA ligase. Competent DG75 was treated with 0.1 μg of the DNA and transformants were selected on L plates containing 50 μg/ml ampicillin. Candidates were screened for the loss of the BamHI restriction site. pOP8 was selected.

To obtain pOP9 the AvaI(repaired)/EcoRI $Tet^R$ fragment from pBR322 was prepared and isolated and ligated to the isolated PvuII(partial)/EcoRI 3560 bp fragment from pOP8.

Ligation of 1.42 kb EcoRI/AvaI(repair) $Tet^R$ (fragment A) and 3.56 kb EcoRI/PvuII $Amp^R$ (fragment B) used 0.5 μg of fragment B and 4.5 μg of fragment A in a two-stage reaction in order to favor intermolecular ligation of the EcoRI ends.

Competent DG75 was transformed with 5 μl of the ligation mixture, and transformants were selected on ampicillin (50 μg/ml) containing plates. pOP9, isolated from $Amp^R$ $Tet^R$ transformants, showed high copy number, colicin resistance, single restriction sites for EcoRI, BamHI, PvuII, HindIII, 2 restriction sites for HincII, and the appropriate size and HaeIII digestion pattern.

To obtain pCS3, 50 μg pEW27 DNA was digested to completion with PvuII and then EcoRI. Similarly, 50 μg of pOP9 was digested to completion with PvuII and EcoRI and the 3.3 kb fragment was isolated.

0.36 μg (0.327 pmoles) pEW27 fragment and 0.35 μg (0.16 pmoles) pOP9 fragment were ligated and used to transform *E. coil* MM294. $Amp^RTet^R$ transformants were selected. Successful colonies were initially screened at 30° C. and 41° C. on beta-lactamase assay plate and then for plasmid DNA levels following growth at 30° C. and 41° C. A successful candidate, designated pCS3, was confirmed by restriction analysis.

G.6 Production of DT-A and DT-A-B' Peptides in *E. coil*

Fresh overnight samples of $pP_L$OPSau, $pP_L$OPMspRT and $pP_L$OPMspCys were inoculated into N8-2 media (per 500 mls: 20 mM $NH_4Cl$, 44 mM $KH_2PO_4$, 56.2 mM $Na_2HPO_4$, 18 mM $K_2SO_4$, 0.4 mM $MgSO_4$, 6 μM $ZnSO_4$, 6 μM $MnSO_4$, 0.2 μM $CuSO_4$, 0.4% glucose, 0.002% thiamine) supplemented with 5 g/l casamino acid, 100 μg/ml ampicillin and 10 μM $FeSO_4$. The cells were grown at 30° C. to an $OD_{680}$ of 0.150, and induced at 60° C. for 45 sec followed by growth at 42° C. for 5 hours. To assess the level of production, 0.5 ml of cells were centrifuged and the pellet was resuspended in 20 μl 3% SDS, 62.5 mM Tris HCl, pH 6.8. Following heating at 95° C. for 5 minutes the samples were run on 12.5% SDS polyacrylamide 3% stacking gel. The results of the polyacrylamide gel electrophoresis of these extracts of transformed cells are shown in FIG. 8.

Lanes 2-9 represent extracts of MC1000-39531 cultures transformed with the plasmids of the invention as follows:

| Lanes 2 and 3 | pP$_L$OPSau |
|---|---|
| Lanes 4 and 5 | pP$_L$OPMspSA |
| Lanes 6 and 7 | pP$_L$OPMspCys |
| Lanes 8 and 9 | pP$_L$OPMspRT | pP$_L$OPMspSA is an expression vector for the Msp fragment extended by an additional 17 amino acids. It is described in a copending application.

Lanes 2, 4, 6 and 8 are extracts of cells which were induced by an increase in medium temperature to 42° C. as described. Lanes 3, 5, 7 and 9 are extracts from uninduced cells.

The quantity of DT-A or DT-A-B' protein produced was assayed in each case by measuring quantitatively the intensity of the relevant protein band illustrated in FIG. 8 upon staining with Coomassie Blue. These intensities corresponded to values of approximately 150 μg/ml cell culture for hosts transformed with pP$_L$OPSau, pP$_L$OPMspRT or with pP$_L$OPMspCys.

The identity of each of the stained bands to the desired DT fragment was confirmed in each case by the EF-2 ADP-ribosylation assay of Chung (supra), and by Western Blot.

H. Expression of IL-2

Native IL-2 is a 133 amino acid sequence with an alanine at its N-terminus. For expression in procaryotic systems, the codons of the leader sequence in the native gene are replaced by an ATG, resulting in production of protein having a methionine residue at the N-terminus. In paragraph H.1 and H.2 below, a 133 amino acid modified IL-2 sequence with N-terminal methionine, lacking the native N-terminal alanine, and containing serine at position 125 designated herein IL-2 des-ala, ser125 is produced under control of the cassette of the invention. Alternate IL-2 constructions employing this cassette, such as that set forth in paragraph H.3, or constructions involving other forms of IL-2 can, of course, be made.

H.1 Construction of pFC54 pFC54 is an expression vector for a modified form of IL-2 wherein the cysteine at position 125 has been replaced by a serine residue (IL-2 des-ala, ser125). It is constructed using pFC5 as a source of the P$_L$N$_{RBS}$ cassette, pLW46 as a source of the coding sequence, and pCS4 as a source of the high copy number replicon, as follows:

pCS4 (see below) and pFC5 (see πD.2) were each digested with EcoRI and HindIII and the digests ligated at 1:2 molar ratio, 60 μg/ml under sticky end conditions. The ligated DNA (150 ng) was used to transform MC1000-39531 to Amp$^R$, and Lac$^-$ transformants were screened for the desired 5.45 kg plasmid. The correct plasmid, pFC8, contained the desired 346 bp EcoRI/HindIII P$_L$N$_{RBS}$ fragment in place of the 110 bp trp control region of pCS4.

pLW46 transformed into E. coli MM294 was deposited 26 September 1983 and assigned ATCC No. 39452. pLW46 was digested to completion with PvuII, HindIII and BanII; pFC8 was digested to completion with HindIII and BanII. The digests were mixed (4:1 molar ratio, 50 μg/ml DNA), ligated under sticky end conditions, and the mixture (100 ng DNA) was used to transform MC1000-39531 to Amp$^R$. Successful transformants were screened for the desired 5.4 kb plasmid lacking a PstI site, containing a unique XbaI site, a unique HindIII site, and yielding a 526 bp EcoRI/XbaI fragment. The desired plasmid was designated pFC54.

pFC54 transformed into E. coli DG95 lambda lysogen was deposited in the CMCC as no. 2015, and was deposited with the ATCC on 4 September 1984 and given accession number 39831.

H.1.a Construction of pCS4 pCS4 was constructed from pCS3 (see para. G.5) by replacing the smaller EcoRI/BamHI digest fragment from pCS3 with an EcoRI/XhoII digest fragment which contains the trp promoter/βIFN coding sequence obtained from the plasmid pβ1trp3-4-1 which was deposited with ATCC 30 March 1984 and has accession no. 39646.

H.2 Production of IL-2 des-ala, ser125 pFC54 was tranformed into E. coli DG95 lambda lysogen and the transformants were grown and induced as set forh in paragraph G.6. These transformants produced IL-2, des-ala, ser125 as 20% of accumulated total cell protein after 1-2 hr of induction at 40° C. The production level was assayed by the intensity of Coomassie Blue stained SDS-polyacrylamide gels. The activity of the IL-2 produced was verified using standard assay methods.

H.3 Construction of pFC53

An IL-2 sequence having 134 amino acid residues, differing from that of paragraph H.1 and H.2 by the presence of an alanine residue (the normal N-terminus in the active sequence) immediately after the methionine encoded by an ATG start codon can be obtained in a manner exactly analogous to that set forth in the previous illustration. The coding sequence for this protein, designated herein IL-2 ser125 is obtained as a HindIII/BanII fragment containing the coding sequence from pLW55. pLW55 in E. coli K12 strain MM294 was deposited with the ATCC 18 November 1983 and given accession number 39516. The resulting plasmid containing the temperature sensitive high copy number replicon from pCS4 and the P$_L$N$_{RBS}$ cassette of the invention from pFC5 was designated pFC53.

Transformation of pFC53 into E. coli DG95 lambda lysogen resulted in cultures which produced IL-2 ser125.

The following plasmids have been deposited at the American Type Culture Collection, Rockville, Md., U.S.A. (ATCC) under the terms of the Budapest Treaty on the International Recognition of the Deposit of Microorganisms for the Purposes of Patent Procedure and Regulations thereunder (Budapest Treaty) and are thus maintained and made available according to the terms of the Budapest Treaty. Availability of such strains is not to be construed as a license to practice the invention in contravention of the rights granted under the authority of any government in accordance with its patent laws.

The deposited plasmids have been assigned the indicated ATCC deposit numbers. The plasmids have also been deposited with the Master Culture Collection (CMCC) of Cetus Corporation, Emeryville, Calif., U.S.A., the assignee of the present application, and assigned the indicated CMCC deposit numbers:

| Plasmid | CMCC No. | ATCC No. | Date of Deposit |
|---|---|---|---|
| pFC54 in E. coli DG95 lambda N7N53cI857 SusP80 lysogen | 2015 | 39831 | 4 September 1984 |
| pβ1-Z15 | 1948 | 39578 | 13 January 1984 |
| pDG141 | 1966 | 39588 | 24 January 1984 |
| pCS3 | | 39142 | 3 June 1982 |
| pβltrp3-4-1 in E. coli MM294 | 1730 | 39646 | 30 March 1984 |

What is claimed is:

1. A portable, regulatable control cassette for expression of a heterologous protein in procaryotic hosts, which cassette comprises:

a first DNA sequence which is the $P_L$ promoter operably linked to a second DNA sequence corresponding to $N_{RBS}$ upstream of a third DNA sequence having a Hind III restriction site which permits cleavage within 6 bp downstream of the $N_{RBS}$ sequence.

2. A portable, regulatable control cassette for expression of a heterologous in procaryotic hosts which cassette comprises:

a first DNA sequence which is the $P_L$ promoter operably linked to a second DNA sequence corresponding to $N_{RBS}$, both aforesaid DNA sequences operably linked to an ATG start codon, all upstream of a third DNA sequence having a restriction site which is not present elsewhere in the cassette and which permits cleavage within 6 bp downstream of the G of the ATG start codon.

3. The cassette of claim 1 which further includes a DNA sequence having a restriction site upstream of the $P_L$ promoter.

4. The cassette of claim 2 which further includes a DNA sequence having a restriction site upstream of the $P_L$ promoter.

5. The cassette of claim 2 wherein the restriction site which permits cleavage within 6 bp downstream of the G of the ATG start codon is a SacI site.

6. The cassette of claim 3 wherein the restriction site upstream of the $P_L$ promoter is an EcoRI site.

7. The cassette of claim 4 wherein the restriction site upstream of the $P_L$ promoter is an EcoRI site.

8. A vector for the expression of a heterologous protein which vector comprises a control cassette which contains:

a first DNA sequence which is the $P_L$ promoter operably linked to a second DNA sequence corresponding to the $N_{RBS}$ and having a restriction site which is not present elsewhere in the cassette which permits cleavage within six base pairs downstream of the $N_{RBS}$ sequence, said cassette operably linked to a DNA sequence coding for said heterologous protein through insertion of the coding sequence at said restriction site, wherein the coding sequence is preceded by an included start codon.

9. The vector for the expression of a heterologous protein which vector comprises the cassette of claim 2 operably linked to a DNA sequence coding for said heterologous protein.

10. The vector of claim 8 which further includes an origin of replication outside of said cassette and said coding sequence which is regulated by temperature.

11. The vector of claim 9 which further includes an origin of replication outside of said cassette and said coding sequence which is regulated by temperature.

12. The vector of claim 9 wherein the heterologous protein is IL-2.

13. The vector of claim 12 wherein the IL-2 is IL-2 des-ala, ser125.

14. The vector of claim 12 wherein the IL-2 is IL-2 ser125.

15. The vector of claim 12 which further includes an origin of replication outside of said cassette and said coding sequence which is regulated by temperature.

16. The vector of claim 13 which is pFC54.

17. The vector of claim 14 which is pFC53.

18. Cells or cell cultures transformed with the vector of claim 9.

19. Cells or cell cultures transformed with the vector of claim 9.

20. A method of enhancing the expression of a heterologous protein which method comprises operably linking the cassette of claim 1 to a DNA sequence, coding for said heterologous protein wherein the coding sequence is preceded by a start codon.

21. A method of enhancing the expression of a heterologous protein which method comprises operably linking the cassette of claim 2 to a DNA sequence coding for said heterologous protein.

22. A method of producing a heterologous protein which comprises culturing the transformed cells of claim 18 and recovering the heterologous protein therefrom.

23. A method for producing a heterologous protein which comprises culturing the transformed cells of claim 19 and recovering the heterologous protein therefrom.

24. The method of claim 23 wherein the heterologous protein is IL-2.

25. The method of claim 24 wherein the IL-2 is IL-2 des-ala, ser125.

26. The method of claim 24 wherein the IL-2 is IL-2 ser125.

* * * * *